US006391868B2

(12) United States Patent
Arnold

(10) Patent No.: US 6,391,868 B2
(45) Date of Patent: May 21, 2002

(54) USE OF 5-ALPHA-ANDROST-1-EN-3, 17-DIONE TO INCREASE THE LEVEL OF THE ANABOLIC/ANDROGENIC HORMONE 17-BETA-HYDROXY-5-ALPHA-ANDROST-1-EN-3-ONE IN HUMANS

(75) Inventor: Patrick Arnold, Seymour, IL (US)

(73) Assignee: LPT Research, Inc., Seymour, IL (US)

( * ) Notice: Subject to any disclaimer, the term of this patent is extended or adjusted under 35 U.S.C. 154(b) by 0 days.

(21) Appl. No.: 09/756,542

(22) Filed: Jan. 9, 2001

Related U.S. Application Data

(63) Continuation-in-part of application No. 09/567,379, filed on May 10, 2000, now abandoned.

(51) Int. Cl.[7] ........................................... A61K 31/5685

(52) U.S. Cl. ....................................................... 514/177

(58) Field of Search ......................................... 514/177

(56) References Cited

U.S. PATENT DOCUMENTS

| 2,441,560 A | * | 5/1948 | Butenandt ................. 260/397.3 |
| 4,877,774 A | | 10/1989 | Pitha et al. .................... 514/26 |
| 5,342,834 A | | 8/1994 | Bardin et al. ................ 514/178 |
| 5,387,583 A | | 2/1995 | Loria ........................... 514/171 |
| 5,578,588 A | * | 11/1996 | Mattern et al. .............. 514/177 |
| 5,880,117 A | | 3/1999 | Arnold ........................ 514/178 |
| 6,117,429 A | * | 9/2000 | Bucci ....................... 424/195.1 |
| 6,011,027 A1 | | 1/2001 | Arnold ........................ 514/182 |
| 6,242,436 B1 | | 6/2001 | Llewellyn ................... 514/177 |

* cited by examiner

*Primary Examiner*—Phyllis G. Spivack
(74) *Attorney, Agent, or Firm*—Maloney, Parkinson & Berns; Michael Berns

(57) ABSTRACT

This invention involves the administration of the natural androgen metabolite 5-alpha-androst-1-en-3,17-dione(1-androstenedione) to produce an androgenic and anabolic response in humans. 1-Androstenedione behaves as a prohormone in vivo, and converts to the active hormone 17-beta-hydroxy-5-alpha-androst-1-en-3-one.

4 Claims, No Drawings

USE OF 5-ALPHA-ANDROST-1-EN-3, 17-DIONE TO INCREASE THE LEVEL OF THE ANABOLIC/ANDROGENIC HORMONE 17-BETA-HYDROXY-5-ALPHA-ANDROST-1-EN-3-ONE IN HUMANS

This application is a continuation-in-part of Ser. No. 09/567,379, filed May 10, 2000, now abandoned.

FIELD OF THE INVENTION

This invention involves the administration of the natural androgen metabolite 5alpha-androst-1-en-3,17-dione(1-androstenedione) to produce an androgenic and anabolic response in humans. 1-androstenedione behaves as a pro-hormone in vivo, and converts to the active hormone 17beta-hydroxy-5alpha-androst-1-en-3-one.

DESCRIPTION OF THE PRIOR ART

U.S. Pat. No. 5,880,117 to Arnold discloses a method of effectively increasing testosterone levels in humans by the administration of the testosterone precursor 4-androstenediol. Similarly, U.S. Pat. No. 6,011,027 to Arnold discloses a method for increasing nortestosterone levels in humans by administration of the nortestosterone metabolic precursor 19-nor-4-androstenediol. In addition to these two patents, U.S. Pat. No. 5,578,588 to Mattern and Hacker also discloses the usage of 4-androstenedione as a metabolic precursor to increase levels of testosterone in humans. The pharmacokinetics of the oral administration of such metabolic precursors is such that a peak in hormone levels in the blood is seen at approximately 90 minutes with a subsequent decline to baseline levels within 3–4 hours. This fact permits one to more closely simulate the natural endogenous pulsatile release of testosterone through multiple daily dosing of androgenic precursors. This should result in a more normal physiological response with a minimization of side effects and HPTA shutdown. Furthermore, since these precursors are not 17alpha alkylated compounds, their hepatotoxicity is minimal.

DESCRIPTION OF THE INVENTION

The steroid hormone testosterone is considered to be the male virilizing hormone. Its effects include maintenance of muscle and bone mass, sexual function, and psychological well being among others. As males grow older, especially after the age of 35, a slow decline in testosterone levels is observed which is accompanied by symptoms that have been associated with the condition known as "andropause." Symptoms of andropause include lethargy, depression, lack of sexual desire and function, and loss of muscle mass and strength.

The steroid hormone 17beta-hydroxy-5alpha-androst-1-en-3-one is a close chemical derivative of testosterone. Chemically speaking it is an analog of testosterone that has the double bond in the 1(2) position instead of the 4(5) position, and an axial hydrogen stemming from carbon 5 of the steroid nucleus. Testosterone's effects on the maintenance of muscle and bone mass are termed anabolic effects, while its effects on the development and maintenance of male sexual organs and male virilization effects (facial hair growth, body hair growth, male pattern baldness, lowering of voice pitch, etc.) are termed androgenic effects. 17beta-hydroxy-5alpha-androst-1-en-3-one differs from testosterone in its therapeutic activity because, although it has been demonstrated to have similar androgenic properties, its anabolic properties are considerably more potent (Steroids (8) 216). This property makes it valuable to those wishing to increase lean body mass, combat osteoporosis, and increase energy levels while minimizing androgenic effects. Examples of persons that would want to minimize androgenic effects would be women, and men with male pattern baldness or prostate problems.

Similar to the prior art, the present invention introduces yet another naturally occurring metabolic precursor to an anabolic/androgenic hormone. 1-androstenedione has been shown to be present as a urinary androgen metabolite in both healthy and diseased men (J.Biol Chem. (182), 299). This compound can interact with the enzyme 17beta-hydroxysteroid dehydrogenase in-vivo to form the active anabolic/androgenic hormone 17beta-hydroxy-5alpha-androst-1-en-3-one. Evidence for this in-vivo conversion exists in the literature. 100 mg of 1-androstenedione given orally to men was found to result in considerable excretion of 17beta-hydroxy-5alpha-androst-1-en-3-one in the urine (J. Steroid Biochem, (3) 933).

Furthermore, 1-androstenedione maintains a unique advantage over other prohormones with 4(5) unsaturation. It is metabolized differently than these other prohormones as it relates to the ultimate degree of formation of 17-keto steroid metabolites. The enzyme 17beta-hydroxysteroid dehydrogenase catalyzes the reversible transformation of the biologically active 17beta-hydroxysteroids to the biologically inactive 17-keto steroids. This reaction is an equilibrium, and for 1(2) unsaturated steroids this equilibrium lies considerably more toward the formation of active 17beta-hydroxysteroids than it does for 4(5) unsaturated steroids (Acta Endocrinologica, (41) 494). As a result, the administration of 1-androstenedione will result in the overall formation of more active 17beta-hydroxyl hormone in the body then 4(5) unsaturated prohormones such as 4-androstenedione, 4-androstenediol, and 19-nor-4-androstenediol will.

Therefore, 1-androstenedione can be used as a superior androgen metabolic precursor to raise levels of 17beta-hydroxy-5alpha-androst-1-en-3-one and impart an anabolic/androgenic response in humans.

1-androstenedione can be given orally in daily doses of 25 to 2000 mg., preferably 100 to 1000 mg. These daily doses can be divided into several subdoses with 2–4 being preferable. In addition to peroral administration, 1-androstenedione can also be effectively administered by several other routes including transdermal, rectal (suppository), intranasal, and sublingual. A particular advantageous method of sublingual administration involves complexing 1-androstenedione with beta-hydroxypropyl-beta-cyclodextrin, which is then pressed into tablets.

Example 1

The favorable 17 keto/17 alcohol equilibrium of 5alpha-ANDROST-1-EN-3,17-DIONE was demonstrated as follows. Chick liver acetone powder was suspended in 0.1 M phosphate buffer (pH7.4), and centrifuged at 5000×gravity. The supernatant solution contained approximately 0.5 grams of tissue per mL, and to this was added either 5alpha-ANDROST-1-EN-3,17-DIONE, or 4-ANDROSTENEDIONE as a suspension in propylene gylcol in such an amount so that the tissue to steroid ration was 1000:1. A Krebs-Ringer solution and 0.002M diphosphopyridine nucleotide were added and the preparations were incubated in air at 38 deg celsius for 30 minutes. The reactions were then stopped by dilution with water and ethyl acetate. The mixtures were then extracted 3 times with ethyl acetate and dried over magnesium sulfate. The extracts were then concentrated down to a small volume and analyzed by gas liquid chromatography. It was seen that the quantity of 17beta-HYDROXY-5alpha-ANDROST-3-EN-3-ONE from the 5alpha-ANDROST-1-EN-3,17-DIONE incubation exceeded the quantity of testosterone from the 4-androstenedione incubation by well over 200%.

Example 2

A 64 year old man with complaints of decreased libido, lethargy, depression, and muscular weakness, was treated for 4 weeks with oral androstenedione 3×100 mg daily. At the end of the 4 weeks he did not report any noticeable improvement in his condition. After a 2 week respite, he then commenced a 4 week regimen of 5alpha-ANDROST-1-EN-3,17-DIONE using the same protocol (3×100 mg daily). After the 4 weeks was completed he reported clearly evident significant improvements in all his symptoms which included marked increases in his exercise capacity.

The foregoing description of the invention are for illustration only. Modifications not included in the description which are obvious to those skilled in the art are intended to be included in the scope of the following claims.

I claim:

1. A method of increasing the 17beta-hydroxy-5alpha-androst-1-en-3-one levels in humans by the administration of an effective amount of 1-androstenedione.

2. The method of claim 1, wherein said administration is peroral.

3. The method of claim 1, wherein said administration is selected from the group consisting of transdermal, rectal, intranasal, and sublingual.

4. The method of claim 1, wherein said amount is a daily dosage of 25 to 2000 mg.

* * * * *